United States Patent [19]

Munechika et al.

[11] Patent Number: 5,662,931
[45] Date of Patent: Sep. 2, 1997

US005662931A

[54] PROCESS FOR PREPARING LIPOSOME COMPOSITION

[75] Inventors: Koji Munechika; Tomoyo Seki; Norihide Kishi; Hiroshi Matsuda; Yasuo Ueda, all of Osaka, Japan

[73] Assignee: The Green Cross Corporation, Osaka, Japan

[21] Appl. No.: 505,180

[22] PCT Filed: Jan. 20, 1994

[86] PCT No.: PCT/JP94/00075

§ 371 Date: Aug. 11, 1995

§ 102(e) Date: Aug. 11, 1995

[87] PCT Pub. No.: WO94/18948

PCT Pub. Date: Sep. 1, 1994

[30] Foreign Application Priority Data

Feb. 23, 1993 [JP] Japan ..................................... 5-056378

[51] Int. Cl.$^6$ ..................................................... A61K 9/127
[52] U.S. Cl. ............................. 424/450; 264/4.1; 264/4.3
[58] Field of Search ............................. 424/450; 264/4.1, 264/4.3

[56] References Cited

U.S. PATENT DOCUMENTS 5,141,674  8/1992  Leigh ..................................... 252/305

*Primary Examiner*—Gollamudi S. Kishore
*Attorney, Agent, or Firm*—Sughrue, Mion, Zinn, Macpeak & Seas

[57] ABSTRACT

The object of the present invention is to provide a process for preparing a drug-containing liposome composition in which (1) a drug to be included into liposomes, particularly a physiologically active protein having a molecular weight of from 500 to 100,000, can be prevented from decomposition and (2) a high rate of drug inclusion can be attained; (3) the resulting liposome composition can be subcutaneously or intramuscularly administered and (4) makes contribution to sustained release of the drug. The process comprises (1) dissolving a lipid in a first organic solvent, (2) adding a drug-containing aqueous solution to the lipid solution, followed by emulsifying to obtain an emulsion, (3) mixing the emulsion at a low temperature with a second organic solvent in which the lipid is sparingly soluble, (4) collecting the precipitated fraction, and (5) suspending the precipitated fraction in an aqueous solvent.

9 Claims, No Drawings

PROCESS FOR PREPARING LIPOSOME COMPOSITION

This application is a 371 of PCT/JP94/00075 filed on Jan. 20, 1994.

FIELD OF THE INVENTION

This invention relates to a process for preparing a drug-containing liposome composition comprising a drug and a lipid.

BACKGROUND OF THE INVENTION

Liposomes composed of a phospholipid have been developed as a drug carrier with high biocompatibility. Intravenous administration of a drug-liposome combination has been studied for the purposes of improving retention of a drug having a short half life in blood or of suppressing deactivation of a drug in a living body. However, liposomes are easily caught by reticuloendothelial cells as well as other colloidal particles and therefore fail to achieve the above purposes.

The rate of drug inclusion into liposomes that has been achieved to date by conventional techniques of liposome preparation is in most cases 50% or lower and this low rate of inclusion has lessened the industrial utility of a drug-liposome composition. To overcome this problem, remote loading techniques and the like have been developed, but those techniques are applicable only to those drugs having a low molecular weight and are charged.

There is a report on experimentation which demonstrates the effect of liposomes in sustaining release of a drug from a drug-liposome composition administered intramuscularly or subcutaneously. Usefulness of liposomes as a carrier in sustained release preparations is known in the art.

JP-A-4-234820 discloses a peptide-liposome composition capable of slowly releasing a peptide having a molecular weight of 500 to 10000 for a long time (at least 14 days). It is assumed that the peptide disclosed has high stability to heat and is stable under the disclosed condition for liposome preparation (the liposome is prepared at the phase transition temperature of the phospholipid used, i.e., 30° C. at the lowest). However, most of physiologically active peptides are labile against heat, and preparation under a low temperature condition is desirable. Additionally, as shown in the Examples to follow, the highest rate of drug inclusion reached by the disclosed technique is no more than 30% in the case of a highly water-soluble drug.

In light of these circumstances, the present inventors conducted extensive study and found, as a result, that (1) a specific process for preparing a liposome composition inhibits decomposition of a drug to be included into liposomes, particularly a physiologically active protein having a molecular weight of 500 to 100,000 (the process per se inhibits the decomposition), (2) that process achieves a high rate of inclusion, (3) the liposome composition prepared by the process can be subcutaneously or intramuscularly administered and (4) the liposome composition makes a contribution to sustained release of the drug. The present invention has been completed based on these findings.

DISCLOSURE OF THE INVENTION

The present invention relates to a process for preparing a drug-containing liposome composition comprising (1) dissolving a lipid in a first organic solvent, (2) adding a drug-containing aqueous solution to the lipid solution, followed by emulsifying to obtain an emulsion, (3) mixing the emulsion at a low temperature with a second organic solvent in which the lipid is sparingly soluble, (4) collecting the precipitated fraction, and (5) suspending the precipitated fraction in an aqueous solvent.

(i) Drug

Drugs which can be used in the present invention particularly include physiologically active proteins having a molecular weight of 500 to 100,000. Examples of such drugs include cytokines, such as interferon (IFN), e.g. IFN-α, IFN-β and IFN-γ, colony-stimulating factors (CSF), e.g., G-CSF, M-CSF, GM-CSF and CSF-HU, calcitonin, and interleukin. Additionally included are plasminogen activators, e.g., urokinase (UK), urokinase precursor, and tissue plasminogen activator (TPA), blood clotting factors FVIII, FIX and FXIII, plasminogen, antithrombin III, $\alpha_1$-antiplasmin, angiotensin, kinin, androsterone, kallikrein, renin, erythropoietin trypsin inhibitor, esterase inhibitor, gonadotropin, progesterone, estrogen, insulin, glucagon, thyroid-stimulating hormone, thyroid hormone, growth hormone, growth factors, and the like.

The drug to be used in the present invention may be a derivative or an active site (fragment) of the above-mentioned physiologically active proteins.

(ii) Lipid

The lipid which can be used in the present invention is not particularly limited as long as it is capable of forming liposomes in which a drug can be incorporated (included), physiologically acceptable, subject to metabolism, and non-toxic. Such lipids include phospholipids, glycolipids, and lipid related compounds.

The phospholipids include phosphatidylcholine, phosphatidylserine, phosphatidic acid, phosphatidylglycerol, phosphatidylethanolamine, phosphatidylinositol, sphingomyelin, dicetyl phosphate, lysophosphatidylcholine (lysolecithin), and mixtures thereof, such as soybean phospholipid and egg yolk phospholipid. Hydrogenated phospholipids may also be used.

The glycolipids include cerebroside, sulfolipid (e.g., sulfatide), and ganglioside.

The lipid related compounds include cholic acid and deoxycholic acid.

The structure of the liposomes may be as a multilamellar vesicle (MLV), a small unilamellar vesicle (SUV), a large unilamellar vesicle (LUV), etc.

(iii) Combining of Drug and Lipid

Combining of a drug and a lipid will be explained by referring to the example where the lipid contains at least a phospholipid.

A lipid is dissolved in a first organic solvent which is capable of dissolving the lipid and is immiscible with water, such as chloroform, dichloromethane or hexane, preferably dichloromethane, to a concentration of about 10 to 1000 mg/ml, preferably about 200 to 1000 mg/ml.

To stabilize the lipid, an antioxidant such as tocopherol (vitamin E) may be added to the solution. A suitable amount of an antioxidant to be added is from about 0.01 to 0.5% by weight based on the weight of the phospholipid. The drug (i) is dissolved in an appropriate aqueous solvent, such as a buffer solution adjusted to pH 4 to 11 (e.g., citrate buffer, phosphate buffer, acetate buffer or physiological saline). The drug solution and the lipid solution are brought into contact with each other, and the mixture is rapidly shaken or agitated. Where a protein is used as drug, it is used in an amount of from 0.01 to 10 parts by weight in terms of protein per part by weight of the phospholipid.

In preparing liposomes, stabilizers such as cholesterol, phosphatidic acid, dicetyl phosphate, stearylamine, and fatty acids (e.g., palmitic acid) may be added.

The liposome composition of the invention may also contain, as a stabilizer, a high molecular weight polymer selected from albumin, dextran, vinyl polymers, nonionic surface active agents, gelatin, and hydroxyethyl starch.

The high molecular weight polymer stabilizer may be incorporated into the liposomes together with a drug and/or be added to the drug-containing liposome composition (i.e., added to the outside of the liposomes). As a matter of course, it may be present both inside and outside the liposomes.

The above-mentioned high molecular weight polymer stabilizer is suitably added in an amount of from 0.5 to 10 parts by weight, preferably 1 to 5 parts by weight, per part by weight of the lipid.

The ratio of the drug-containing aqueous solution to the lipid-organic solvent solution is from about 1/10 to 1/! t preferably from about 1/10 to 1/2, by volume.

The emulsification of the lipid-organic solvent solution and the drug-containing aqueous solution is carried out at a temperature not higher than room temperature.

The thus prepared O/W emulsion is mixed with a second organic solvent in which the lipid is sparingly soluble at a low temperature, for example, 10° C. or lower, to form a precipitate. It is preferable to use the second organic solvent previously cooled to 10° C. or lower. If desired, the emulsion may also be cooled beforehand. The second organic solvent should be sparingly capable of dissolving the lipid to such an extent that the mixed system forms a precipitate at a prescribed temperature and is preferably immiscible with water. Such organic solvents include ethyl acetate and acetone, with ethyl acetate being preferred. The second organic solvent is used in an amount at least equal to, preferably 5 times or more, the volume of the emulsion.

Then, the precipitated fraction, which contains a drug-lipid complex mainly comprising drug-containing liposomes, is collected, for example, by centrifugation.

The collected fraction is suspended in an appropriate aqueous solvent to obtain a liposome composition according to the present invention. Suitable aqueous solvents include physiological saline and buffers (e.g., phosphate buffer and citrate buffer). The aqueous solvent is used in an amount of at least 0.5 part, preferably at least 1 part, by weight per part by weight of the precipitate fraction.

The resulting drug-containing liposome composition usually has a liposome diameter of about 10 nm to 50 μm, preferably 50 nm to 20 μm.

In the drug-containing liposome composition of the present invention, the drug is present mainly in the liposomes but may be present in the aqueous phase outside the liposomes. The rate of inclusion (i.e., the ratio of a drug included in the liposomes to the total drug present in the drug-containing liposome composition) is not less than 30% by weight, preferably not less than 50% by weight.

If desired, the drug-containing liposome fraction may be isolated from the composition and purified through known means, such as centrifugation and gel filtration.

The drug-containing liposome composition or the liposome fraction thereof may be washed with a pharmaceutically acceptable aqueous solution if desired, divided in portions and formulated into pharmaceutical preparations, in the form of liquid, pellets or suspensions. The preparation is carried out in accordance with the widely known methods in the art of pharmaceutical preparation. The liquid preparations may be frozen followed by drying under reduced pressure to prepare lyophilized preparations.

The dose of the preparation can be adjusted according to the conditions, symptoms, the body weight or age of a patient, etc. The preparation can be administered, for example, intramuscularly or subcutaneously.

BEST MODE FOR CARRYING OUT THE INVENTION

The present invention will be explained in greater detail with reference to Examples and Test Examples, but the present invention should not be construed as being limited thereto. The following abbreviations are used in Examples and Test Examples.

EPC: egg phosphatidylcholine

MLV: multilamellar vesicle

SA: stearylamine

EXAMPLE 1

Preparation of Liposomes

A hexane-ethanol solution containing 800 mg of EPC was put in an egg-plant type flask and dried at room temperature under reduced pressure. Two ml of dichloromethane was put in the flask to dissolve EPC, and 0.5 ml of an aqueous solution of IFN-α ($10^5$ unit/ml) was added to the solution, followed by emulsifying by means of Biotron (a mechanical mixer). The resulting emulsion was poured into 20 ml of ethyl acetate cooled with dry ice-ethanol, and the precipitate formed was collected by centrifugation (10,000 g×10 min). The collected precipitate fraction comprising a drug-EPC complex was suspended in 20 ml of a buffer or physiological saline to obtain a liposome composition of the present invention.

Gel Filtration

The above prepared liposome composition was subjected to gel filtration as follows. Gel filtration was conducted using a column (1.0 cm diameter×18 cm length) packed with Sephacryl S-400 gel and equilibrated with a gelatin-containing tris buffer (pH 7.4). The liposome fractions that eluted at the void volume were collected.

EXAMPLE 2

A liposome composition was prepared in the same manner as in Example 1, except for replacing EPC with a 4:1 mixture of EPC and SA.

EXAMPLE 3

A liposome composition was prepared in the same manner as in Example 1, except for replacing IFN-α with a UK precursor.

TEST EXAMPLE 1

The rate of drug inclusion in the liposome composition prepared in Example 1 was 61%. That is, 61% of the drug was present in the liposome fraction, and 39% of the drug was present in the outer aqueous phase. The liposomes had an average particle size of 4.6 μm.

On the other hand, a lipid thin membrane of EPC was prepared in accordance with a conventional process (JP-A-

3-63298), and an aqueous solution of IFN-α was added and suspended to prepare MLV. The rate of drug inclusion was 25%.

TEST EXAMPLE 2

The liposome composition prepared in Example 1 (IFN-α: 200 μg/ml) was subcutaneously administered to the back of a 7-week-old male BALB/c mouse weighing 25 g at a dose of 0.1 ml. After 120 hours from the administration, the mouse was sacrificed with a chemical, blood was taken from the heart, and the plasma was separated. The site of administration was excised and minced in 1 ml of 1% Triton X-100, and the drug remaining in the site of administration was extracted.

As a control, a 200 μg/ml solution of the drug in physiological saline was used. The drug concentration in the plasma and the tissue extract was measured by ELISA.

As a result, it was found that the drug concentration in plasma was 0.26 ng/ml (that of the control was 0 ng/ml) and the drug retention at the site of administration was 24% (that of the control was 0%). Therefore, the liposome composition of the present invention is expected to be useful as a sustained release preparation.

Industrial Applicability

As compared with a drug per se, the drug-containing liposome composition of the present invention suppresses disappearance of the drug in a living body, especially in blood, thereby maintaining the drug level in blood.

Accordingly, the liposome composition enhances the pharmacological activity of the drug in addition to the property possessed by the drug itself.

According to the liposome composition prepared by the process of the present invention, decomposition of the drug, particularly a physiologically active substance, can be inhibited, a high rate of drug inclusion can be attained, the resulting preparation can be administered subcutaneously or intramuscularly, and thus makes contribution to sustained release of the drug.

We claim:

1. A process for preparing a drug-containing liposome composition comprising the following steps: (1) dissolving a lipid capable of forming liposomes in which a drug can be incorporated in a first organic solvent to form a lipid solution, (2) adding a drug-containing aqueous solution to the lipid solution, followed by emulsification to obtain an emulsion, (3) mixing the emulsion with a second organic solvent in which the lipid is sparingly soluble, (4) collecting precipitates formed in step (3), and (5) suspending the precipitates in an aqueous medium.

2. The process according to claim 1, wherein the first organic solvent dissolves the lipid and is immiscible with water.

3. The process according to claim 1, wherein the first organic solvent is selected from the group consisting of chloroform dichloromethane and hexane.

4. The process according to claim 1, wherein the second organic solvent is selected from the group consisting of ethyl acetate and acetone.

5. The process according to claim 1, wherein the second mixed emulsion is immiscible with water.

6. The process according to claim 1, wherein the drug is a physiologically active protein having a molecular weight of from 500 to 100,000.

7. The process according to claim 1, wherein step (3) is carried out at a temperature of not higher than 10° C.

8. The process according to claim 1, wherein the lipid is selected from the group consisting of phospholipids and glycolipids.

9. The process according to claim 1, wherein the lipid is a phospholipid.

* * * * *